United States Patent [19]

Asao

[11] Patent Number: 4,634,513
[45] Date of Patent: Jan. 6, 1987

[54] APPARATUS FOR RECOVERING FRACTIONATED SAMPLE FROM GEL

[75] Inventor: Jezro Asao, Tokyo, Japan

[73] Assignee: Funakoshi Pharmaceutical Co., Ltd., Tokyo, Japan

[21] Appl. No.: 727,504

[22] Filed: Apr. 26, 1985

[30] Foreign Application Priority Data

Jul. 28, 1984 [JP] Japan .............................. 59-156515

[51] Int. Cl.$^4$ ........................................... G01N 27/28
[52] U.S. Cl. ................................ 204/301; 204/182.8; 204/299 R
[58] Field of Search ............. 204/182.8, 182.9, 299 R, 204/182.7, 182.6, 182.4, 301, 182.3

[56] References Cited

U.S. PATENT DOCUMENTS

| | | | |
|---|---|---|---|
| 2,863,813 | 12/1958 | Juda et al. | 204/182.4 |
| 3,255,100 | 6/1966 | Raymond | 204/182.1 |
| 3,341,441 | 9/1967 | Giuffrida et al. | 204/182.4 |
| 3,930,880 | 1/1976 | Hoefer | 204/182.8 X |
| 3,989,612 | 11/1976 | Kragt et al. | 204/182.8 X |
| 4,049,534 | 9/1977 | Posner | 204/299 R |
| 4,149,957 | 4/1979 | Gibson et al. | 204/301 |
| 4,159,933 | 7/1979 | Allington et al. | 204/299 R X |

OTHER PUBLICATIONS

EpiGene catalog.

Primary Examiner—John F. Niebling
Assistant Examiner—B. J. Boggs, Jr.
Attorney, Agent, or Firm—Flynn, Thiel, Boutell & Tanis

[57] ABSTRACT

An apparatus for efficiently recovering from gel fractionated sample in a short period of time comprises a rotatable vessel which is provided in a tank to be applied with electricity and which is made of dialysis membrane on its side and a reticulate support plate which is fixed inside the vessel independently of and not contacting the vessel. As the vessel is rotated with solvent solution being charged in the tank and the vessel and gel being charged in the reticulate support plate, direct current is passed between the positive and the negative electrodes provided on both sides of the tank. The direction of the current is thereby reversed at every 180° of rotation of the vessel, such that the fractionated sample eluted into the solvent solution by electrophoresis is forced to remain inside the vessel for efficient recovery thereof.

4 Claims, 3 Drawing Figures

APPARATUS FOR RECOVERING FRACTIONATED SAMPLE FROM GEL

BACKGROUND OF THE INVENTION

The present invention relates to an apparatus for recovering a fractionated sample from a support gel by eluting the same into a solution by electrophoresis and the like method, wherein agar or acrylamide gel is employed as the support gel.

DISCLOSURE OF THE PRIOR ART

Prior art methods for recovering, from a gel, a fractionated sample by eluting the same into a solution include a method of leaving in a solution a gel strip containing fractionated sample to diffuse the same, or of blocking the gel in the solution by means of a dialysis membrane and by passing the direct current therethrough.

These prior art methods are defective in that recovery of the fractionated sample takes an extended period of time, or that the yield of recovery is inadequately low.

SUMMARY OF THE INVENTION

The present invention therefore aims to provide an apparatus for a complete recovery, from a gel, of the fractionated sample in a solvent in a short time, and more particularly to an apparatus comprising a tank which is to be applied with electric current and has positive and negative electrodes on both sides thereof, a vessel which is made of a dialysis membrane and which is positioned rotatably between said positive and negative electrodes, and a reticulate support plate which contains the gel and is provided inside said vessel independently of and not contacting the same. In operation, the direct current is passed between said positive and negative electrodes while the vessel is rotated.

According to the present invention, the fractionated sample is eluted by electrophoresis into a solvent solution contained in said vessel. As the vessel is rotated, the direction in which the electric current passes through the membrane is reversed at every 180° of rotation, the fractionated sample is forced to remain inside the vessel, enabling efficient recovery of the same in a shorter period of time.

Other advantages, features and construction of the present invention will be more easily understood from an embodiment described below with reference to the accompanying drawing.

DESCRIPTION OF THE PREFERRED EMBODIMENT

Figure 1:
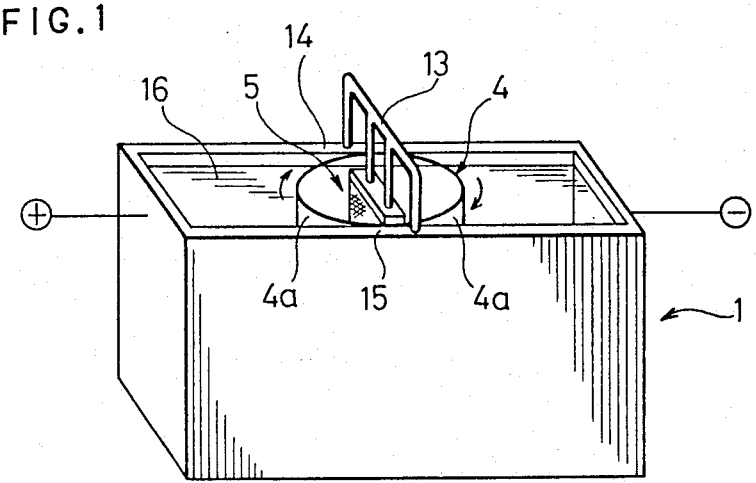
FIG. 1 is an overall perspective view of an embodiment according to the present invention.
Figure 2:
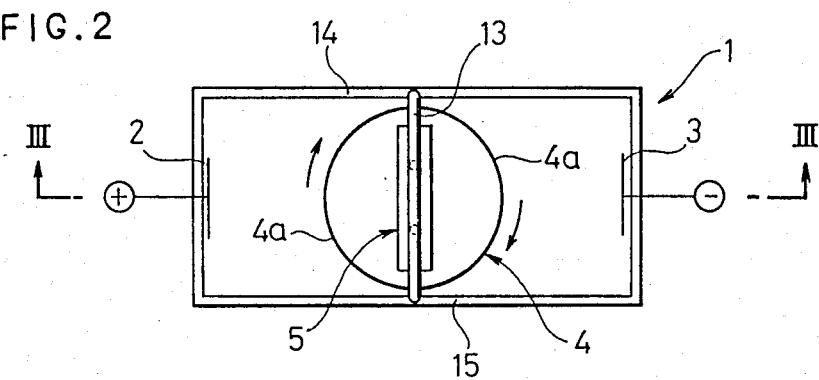
FIG. 2 is a plan view of FIG. 1.
Figure 3:
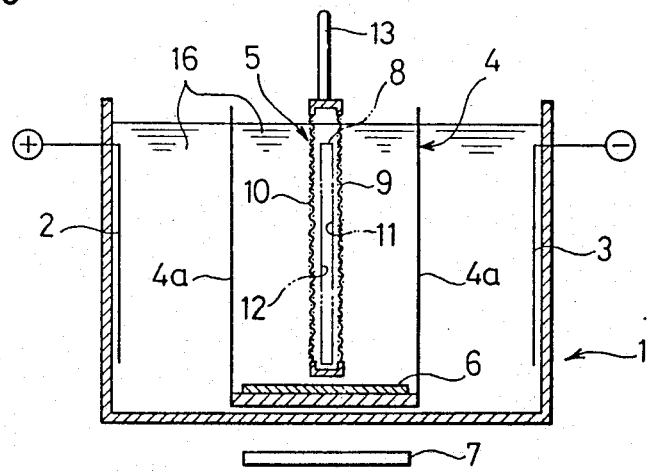
FIG. 3 is a sectional view of FIG. 2 taken along the line indicated by the arrows III—III.

A tank 1 to be applied with electric current is shaped like a box and is provided with a positive electrode 2 and a negative electrode 3 adjacent opposite sides thereof. A vessel 4 is rotatably provided between the positive electrode 2 and the negative electrode 3. The vessel 4 is shaped like a cylinder, its sidewall is made of a dialysis membrane 4a and it has an open top and a closed bottom, to which a magnet member 6 is attached. Magnetic Stirrer 7 (tradename) is provided outside the tank 1 at a position corresponding to the magnet member 6 so that the vessel 4 can be rotated via the magnet 6 utilizing the magnetic field.

Inside the vessel 4 of the above construction is positioned a reticulate support plate 5. The reticulate support plate 5 contains a gel strip which in turn contains the fractionated sample to be recovered. The reticulate support plate is positioned inside the vessel 4 independently of and not contacting the same in such a manner that the surfaces 9 and 10 of the support plate 5 are opposed respectively to the positive electrode 2 and the negative electrode 3. The gel strip 8 is positioned inside the reticulate support plate 5 so that its surfaces 11 and 12 are respectively opposed to the surfaces 9 and 10 of the reticulate support plate 5. Thus the gel strip 8 is supported and fixed direction-wise so that the distance of electricity flow and of electrophoresis within the strip become shorter.

In order to position the reticulate support plate 5 inside the vessel independently of and not contacting the same, a rack 13 is removably attached to the tank 1 on both of its side walls at their respective top edges. The reticulate support plate 5 is suspended from the rack 13. Both the tank 1 to be applied with electric current and the vessel 4 are constructed in such a way as to contain a solvent solution.

Operation of the apparatus having the above construction will now be explained.

A solvent solution 16 is charged into the tank 1 and the vessel 4 respectively and the gel strip 8 containing the fractionated sample is placed in the reticulate support plate 5. When the vessel 4 is rotated at a suitable rate and the direct current is applied between the positive and negative electrodes 2 and 3, the fractionated sample in the gel strip 8 is subjected to electrophoresis to be eluted into the solvent solution 16. In the course of elution, however, the fractionated sample is blocked by the dialysis membrane 4a and remains in the vessel 4.

According to the present invention, clogging of the fractionated sample in the pores of the dialysis membrane 4a as it moves in the direction toward the electrode can be avoided. In other words, as the vessel 4 is structured to rotate, the direction of the current with respect to the dialysis membrane 4a is reversed at every 180° of rotation and the fractionated sample is forced to constantly stay inside the vessel 4. As a result, increase in the electric resistance and heat generation in the pores of the dialysis membrane 4a can be reduced and the fractionated sample is less likely to be modified.

The fractionated sample eluted in the solvent solution contained in the vessel 4 can be recovered using the apparatus of the above construction at a higher efficiency and in a shorter time.

The apparatus according to the present invention is in no way restricted by the embodiment mentioned above, and it can be modified freely within the scope and spirit of the invention.

What is claimed is:

1. An apparatus for recovering an electrophoretically fractionated sample from a gel strip containing the same, which comprises:

a tank; a positive electrode and a negative electrode disposed inside said tank in spaced-apart relationship and adapted to be connected to the positive and negative terminals, respectively, of a direct current power source; a rotatable, cylindrical vessel disposed in said tank between and spaced from said electrodes, said vessel having a cylinderical sidewall made of a dialysis membrane; means for rotating said vessel with respect to said tank; and a stationary, reticulate support disposed within said vessel and spaced therefrom so that said reticulate support remains stationary when said vessel is rotated with respect to said tank, said reticulate support having a cavity for containing a gel strip containing a fractionated sample so that the gel strip remains stationary when said vessel is rotated with respect to said tank, whereby when the tank and the vessel are charged with a solvent solution, said vessel is rotated and direct current is flowed between said positive and negative electrodes, the fractionated sample is subjected to electrophoresis, is eluted into the solvent solution in the vessel and remains in the vessel.

2. The apparatus as claimed in claim 1 in which said reticulate support is comprised of two, spaced-apart, planar, reticulate surfaces which are opposed to said positive and negative electrodes, respectively, said surfaces defining therebetween said cavity for containing the gel strip.

3. The apparatus as claimed in claim 2, including a rack removably attached to the wall of the tank and extending across said tank above said vessel, said reticulate support being suspended from said rack so that it is removably fixed inside said vessel and is independent of and does not contact said vessel.

4. The apparatus as claimed in claim 1 in which the means for rotating said vessel comprises a magnetic drive unit outside said tank and a magnet member connected to said vessel and adapted to be rotated by said magnetic drive unit.

* * * * *

UNITED STATES PATENT AND TRADEMARK OFFICE
CERTIFICATE OF CORRECTION

PATENT NO. : 4 634 513
DATED : January 6, 1987
INVENTOR(S) : Tezro Asao

It is certified that error appears in the above-identified patent and that said Letters Patent is hereby corrected as shown below:

On the title page, at item [75], change the first name of the inventor to ---Tezro---.

Signed and Sealed this

Eighteenth Day of August, 1987

*Attest:*

DONALD J. QUIGG

*Attesting Officer*  *Commissioner of Patents and Trademarks*